(12) United States Patent  (10) Patent No.: US 8,103,353 B1
Karunasiri  (45) Date of Patent: *Jan. 24, 2012

(54) DIGITALLY CONTROLLED RF AMPLIFIER WITH WIDE DYNAMIC RANGE OUTPUT

(75) Inventor: Rankiri T. Karunasiri, Castaic, CA (US)

(73) Assignee: Advanced Bionics, LLC, Valencia, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 12/782,007

(22) Filed: May 18, 2010

Related U.S. Application Data

(62) Division of application No. 11/341,806, filed on Jan. 27, 2006, now Pat. No. 7,751,902.

(51) Int. Cl.
*A61N 1/36* (2006.01)
(52) U.S. Cl. ........................................................ 607/55
(58) Field of Classification Search .................. 607/136, 607/137, 55–57, 33, 61, 32, 60
See application file for complete search history.

(56) References Cited

U.S. PATENT DOCUMENTS

| | | | |
|---|---|---|---|
| 3,751,605 A | 8/1973 | Michelson | |
| 4,400,590 A | 8/1983 | Michelson | |
| 4,532,930 A | 8/1985 | Crosby et al. | |
| 4,592,359 A | 6/1986 | Galbraith | |
| 4,947,844 A | 8/1990 | McDermott | |
| 5,083,094 A * | 1/1992 | Forsberg | 330/124 R |
| 5,741,314 A * | 4/1998 | Daly et al. | 607/60 |
| 5,824,022 A | 10/1998 | Zilberman et al. | |
| 7,016,738 B1 * | 3/2006 | Karunasiri | 607/57 |
| 7,254,449 B2 * | 8/2007 | Karunasiri | 607/61 |

OTHER PUBLICATIONS

Non-Final Office Action received in related U.S. Appl. No. 11/341,806 on Aug. 25, 2009.

* cited by examiner

*Primary Examiner* — George Evanisko
(74) *Attorney, Agent, or Firm* — AdvantEdge Law Group, LLC

(57) ABSTRACT

A push-pull amplifier efficiency provides a 4:1 (12 dB) course adjustment of power output by using a single digital control input. The amplifier is provided with an input voltage (VDD) having sixteen steps ranging from 1.25 volts to 3.00 volts. Based on the digital control, an integrated circuit switches between a high power mode and a low power mode. In the low power mode, the output voltage is equivalent to the input voltage. In the high power mode, the amplifier provides an output of twice the input voltage (or four times the power).

9 Claims, 9 Drawing Sheets

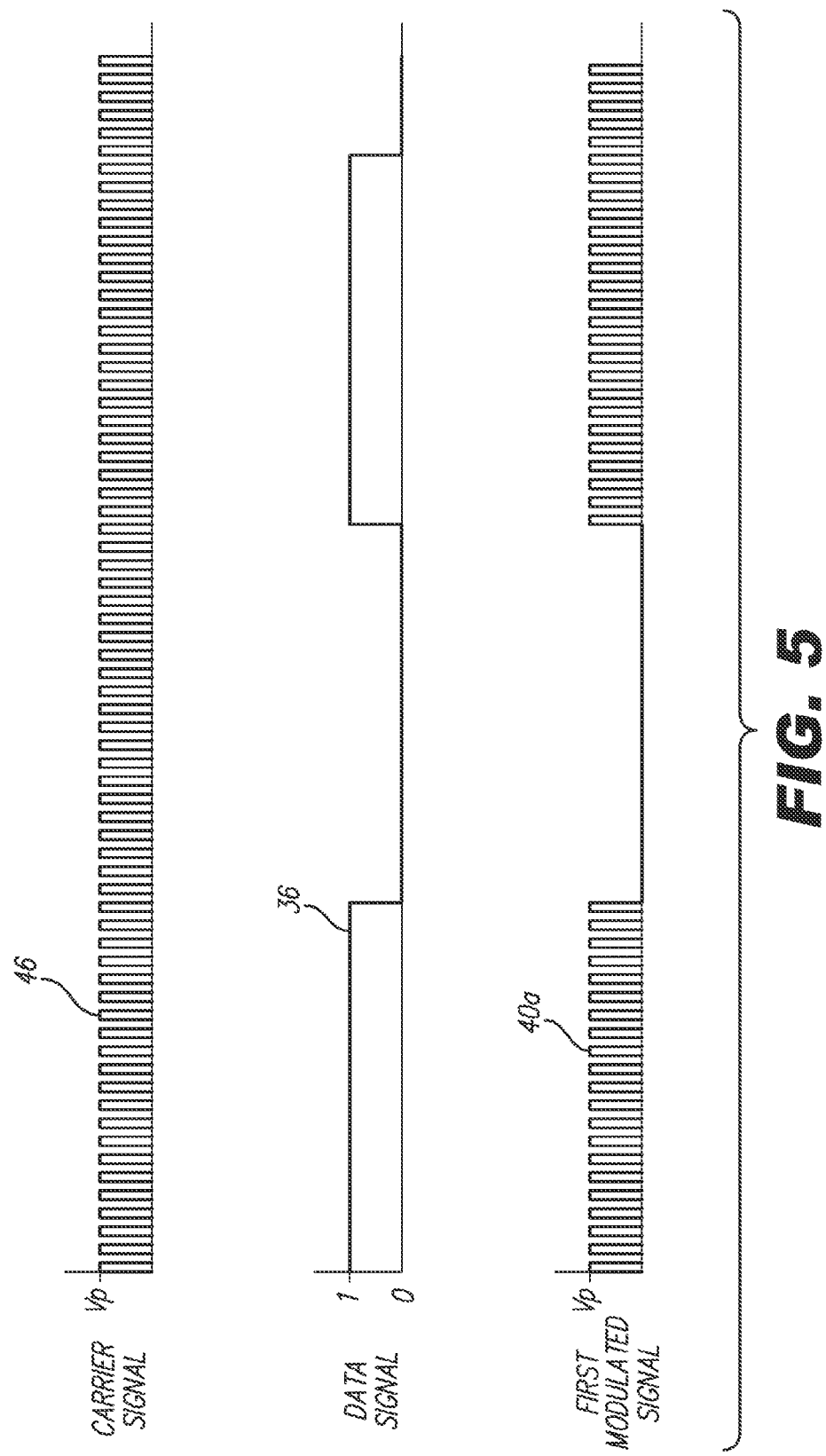

DIGITALLY CONTROLLED RF AMPLIFIER WITH WIDE DYNAMIC RANGE OUTPUT

RELATED APPLICATIONS

The present application is a divisional application of U.S. patent application Ser. No. 11/341,806, filed Jan. 27, 2006, which application is a divisional application of U.S. Pat. No. 7,016,738. Both applications are incorporated herein by reference in their entireties.

BACKGROUND

The present invention relates to battery powered implantable devices, and in particular to an improved Radio Frequency (RF) power amplifier for Implantable Cochlear Stimulator (ICS) systems. Such ICS systems provide improved hearing for the hearing impaired. The RF power amplifier serves the important function of providing power to the implanted part of the ICS system and the efficiency of the RF power amplifier is crucial in developing the miniaturized systems of the future.

U.S. Pat. No. 4,400,590 issued Aug. 23, 1983 for "Apparatus for Multi-Channel Cochlear Implant Hearing Aid System" describes and illustrates a system for electrically stimulating predetermined locations of the auditory nerve within the cochlea of the ear, which system includes a multi-channel intra-cochlear electrode array positioned adjacent to the auditory nerve within the cochlea of the ear. The electrode array comprises a plurality of exposed electrode pairs spaced along and embedded in a resilient curved base for implantation in accordance with the method of surgical implantation described in U.S. Pat. No. 3,751,605 issued Aug. 7, 1973 for "Method of Inducing Hearing." The hearing aid system described in the '590 patent includes a signal processor located outside the body of a hearing impaired patient. The signal processor receives audio signals (i.e., sound waves) and converts the audio signals into analog data signals which are carried by a lead through the patient's skin to the implantable multi-channel intra-cochlear electrode array. The analog signals are applied to selected ones of the plurality of exposed electrode pairs included in the intra-cochlear electrode array to electrically stimulate predetermined locations of the auditory nerve.

U.S. Pat. No. 4,532,930, issued Aug. 6, 1985 for "Cochlear Implant System For an Auditory Prosthesis" describes and illustrates a multiple electrode system which does not employ a lead passing through the skin. Though multiple electrodes are employed to stimulate hearing, the system only operates with a single pulsatile output stimulating a single electrode channel at any given time. Such a sequential system is limited in speed of operation, and does not provide for analog operation where continuous stimulating signals, controllable in amplitude, are simultaneously applied to a number of electrode channels. Further, the system is subject to charge imbalance with misprogramming or circuit fault and inefficient use of electrical power. Moreover, once the stimulator unit is implanted there are no means for monitoring its ongoing circuit operation or power requirements so as to optimize its continued operation.

U.S. Pat. No. 4,592,359, issued Jun. 3, 1986 for "Multi-Channel Implantable Neural Stimulator" describes a cochlear implant system having 4 current sources and 4 current sinks per channel, controlled by series switches, to provide 16 different circuits for supplying 16 levels of 2 polarities to each output channel. In a pulsatile mode, the system provides for simultaneous update (amplitude control) and output to all channels. However, the system does not permit simultaneous analog update and output on all channels and the electrode pairs for each channel are not electrically isolated from all other electrode pairs whereby undesired current leakage may occur. Further, once the stimulator is implanted there are no means for monitoring its ongoing circuit operation or power requirements so as to optimize its continued operation.

U.S. Pat. No. 4,947,844, issued Aug. 14, 1990 for "Receiver/Stimulator For Hearing Prosthesis" describes and illustrates a multiple channel electrode system. The system includes an implantable receiver/stimulator connected to an implantable electrode array. Included in the implantable receiver/stimulator is a transmitter for telemetering one electrode voltage, measured during stimulation, to an external receiver for monitoring and analysis as an indicator of proper operation of the implantable stimulator. The transmitter comprises an oscillator operating at a frequency of about 1 MHz. The output of the oscillator is coupled to the implant's receiving coil. The oscillator signal, when received after transmission, is demodulated to recover the selected voltage waveforms.

Recently, ICS systems have been introduced which include a behind-the-ear speech processor, e.g., of the type described in U.S. Pat. No. 5,824,022 issued Oct. 20, 1998 for 'Cochlear Stimulation System Employing Behind-The-Ear (BTE) Speech Processor with Remote Control.' BTE speech processors offer several advantages, but because of their small size, BTE speech processors are limited in the size of the battery they may carry (which in turn limits the useful life of the battery.) The small battery size results in a requirement for very low power consumption. Further, known BTE external devices may be required to cooperate with two or more varieties of implantable devices. Such varieties of implantable devices have significantly different power requirements, and techniques such as dynamic output power control have been used to meet the varying power requirements. Unfortunately, known methods of dynamic output power control fail to produce consistent voltage output when required to operate over a wide range of voltages. Specifically, the threshold voltage of amplifiers with MOS transistors may limit the minimum voltage the amplifier can produce with adequate output voltage control.

What is needed is an RF amplifier with a wide dynamic range, suitable for use in an ICS system.

SUMMARY

The present invention addresses the above and other needs by providing an RF amplifier with a 4:1 (12 dB) course adjustment of power output, which course adjustment is controlled by a single digital control input. The RF amplifier is provided with an input voltage ($V_{DD}$) having sixteen steps ranging from 1.25 volts to 3.00 volts. Based on the digital control, an integrated circuit switches between a high power mode and a low power mode. In the low power mode, the output voltage is a modulated version of the input voltage. In the high power mode, the amplifier provides an output that is a modulated version of twice the input voltage (or four times the power). The RF amplifier includes a transformer-coupled output-matching network. To operate in the low power mode, a first modulated signal is input to a first output driver, to produce a first push-pull output between 0 and $V_{DD}$, resulting in a $V_{DD}$ voltage swing through a primary coil. To operate in the high power mode, the first modulated signal is input to the first output driver, to produce the first push-pull output modulated between 0 and $V_{DD}$, and a second modulated signal (a 180 degrees phase shifted version of the first modulated signal) is input to a second output driver, to produce an opposing second push-pull output modulated between 0 and $V_{DD}$, resulting in a $2 V_{DD}$ voltage swing through the primary coil.

In accordance with one aspect of the invention, there is provided an improved RF amplifier for an Implantable Cochlear Stimulation (ICS) system that may be switched between a low power mode and a high power mode, to efficiently provide power to different implantable devices having different power requirements. There is a desire to have a single external device capable of interfacing with two or more electronically different implantable devices. In one example, a first implantable device has a power requirement range from 50 to 200 mW, and a second implantable device has a power requirement range from 10 to 90 mW. Known methods for controlling power over the range from 10 to 200 mW may result in a failure to provide an efficient output at very low power levels. The RF amplifier of the present invention provides a 4:1 course adjustment of output power to meet the requirements of both a high power requirement implantable device, and a low power requirement implantable device, and thereby retains the ability to efficiently control the power output at low power levels.

It is a further feature of the present invention to provide a 4:1 course output power adjustment through digital control while avoiding a complicated hardware solution. The RF amplifier of the present invention comprises a transformer-coupled output-matching network which may be digitally switched between a high power push-pull configuration to obtain twice the supply voltage, and a low power mode operating at the supply voltage.

BRIEF DESCRIPTION OF THE DRAWINGS

The above and other aspects, features and advantages of the present invention will be more apparent from the following more particular description thereof, presented in conjunction with the following drawings wherein:

FIG. 5 depicts a carrier signal, a data signal, and a resulting modulated signal;

Corresponding reference characters indicate corresponding components throughout the several views of the drawings.

DETAILED DESCRIPTION

Figure 1:
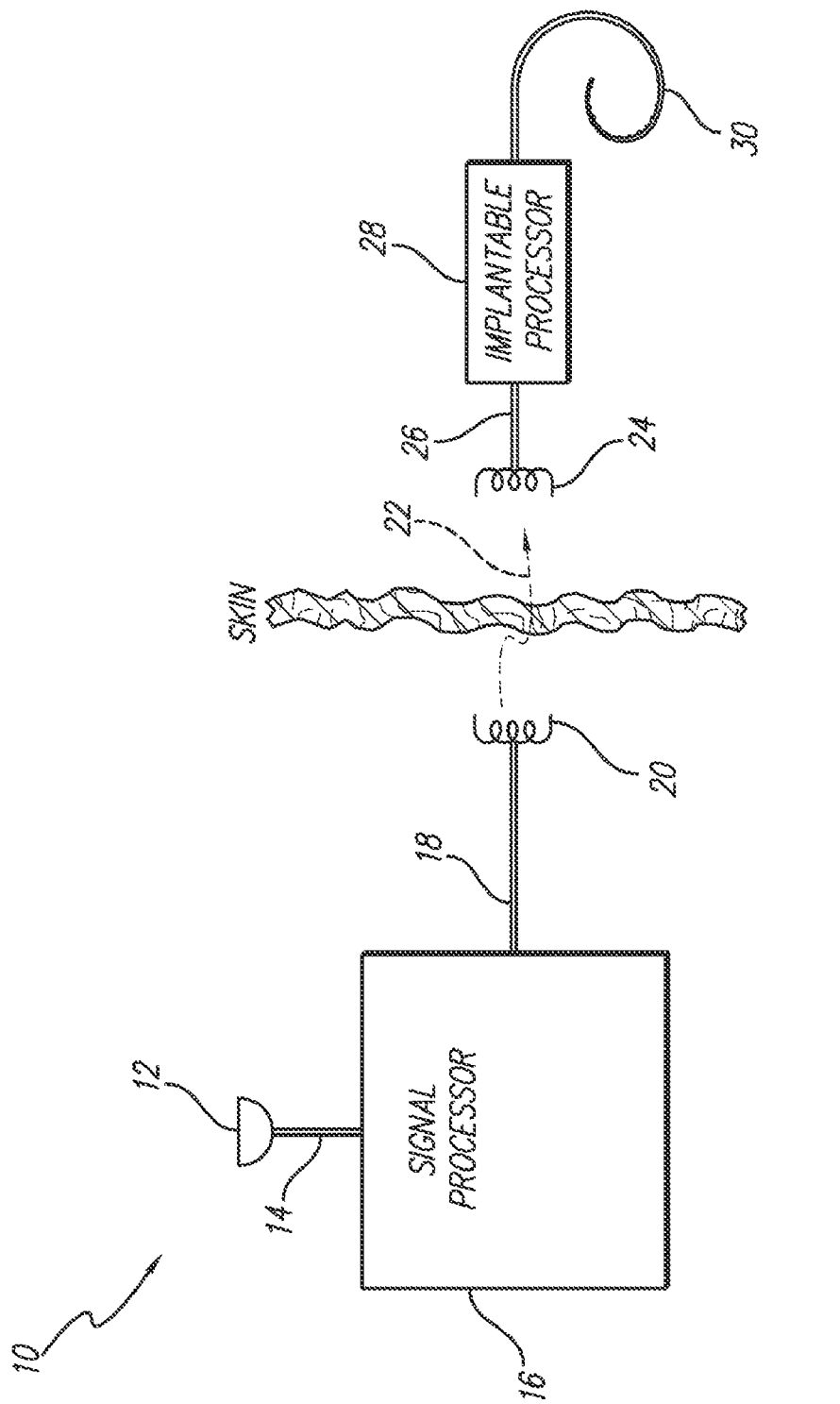
FIG. 1 shows elements of an Implantable Cochlear Stimulation (ICS) system suitable for application of an RF amplifier according to the present invention.

The following description is of the best mode presently contemplated for carrying out the invention. This description is not to be taken in a limiting sense, but is made merely for the purpose of describing the general principles of the invention. The scope of the invention should be determined with reference to the claims.

Implantable Cochlear Stimulation (ICS) systems 10 have been developed to provide the sensation of hearing to the hearing impaired. An exemplary ICS system 10 shown in FIG. 1 includes a microphone 12 for converting acoustic energy into an electrical signal, a signal processor 16 for processing the electrical signal to generate a processed signal, a microphone lead 14 for carrying the electrical signal from the microphone 12 to the signal processor 16, a primary antenna 20 for transmitting the processed signal over a Radio Frequency (RF) link 22, a primary coil lead 18 for carrying the processed signal from the Signal Processor 16 to the primary antenna 20, a secondary antenna 24 for receiving the processed signal transmitted over the RF link 22, an implantable processor 28 for processing the received signal to generate a stimulation signal, a secondary coil lead 26 for carrying the processed signal from the secondary antenna 24 to the implantable processor 28, and an implantable electrode array 30 for providing the stimulation signal to nerves in the cochlea.

Figure 2:
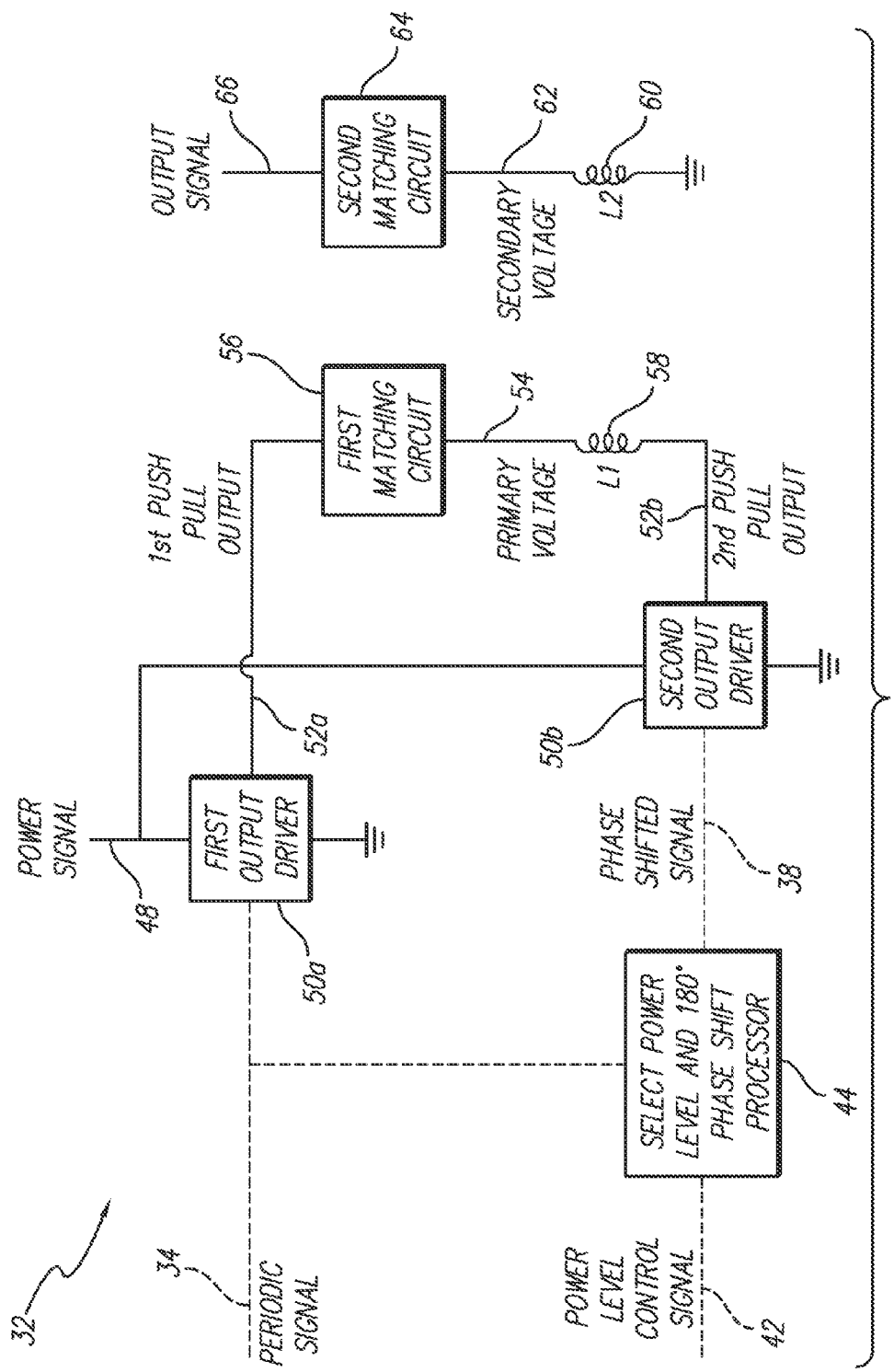
FIG. 2 shows a digitally controlled amplifier providing a wide dynamic range.

Some electrical devices require a power supply with wide dynamic range. A digitally controlled amplifier 32 with a course voltage adjustment providing a wide dynamic range is shown in FIG. 2. The amplifier receives a DC power signal with voltage Vp, and produces an power output at either Vp or twice Vp, thereby providing a 4:1 course power adjustment. A periodic signal 34 is preferably a square wave between zero and Vs, or may be another waveform which sufficiently swings above and below the input thresholds of subsequent processing elements (e.g., output drivers). The signal 34 is provided to a first output driver 50a and to a Select Power Level and 180 Degree Phase Shift Processor (hereafter, level and phase processor) 44. A power level control signal 42 is also provided to the level and phase processor 44. The signal 42 indicates if the amplifier 32 is in a high power mode or in a low power mode. In the low power mode, the level and phase processor 44 generates a phase shifted signal 38 set to zero. In the high power mode, the level and phase processor 44 generates a phase shifted signal 38 set to the signal 34 with a 180 degree phase shift. The signal 38 is provided to a second output driver 50b.

The first output driver 50a generates a first push pull output 52a by amplifying the signal 34 (i.e., generating an amplified replica of the signal 34). The second output driver 50b similarly generates a second push pull output 52b by amplifying the signal 38 (i.e., generating an amplified replica of the signal 38). The push-pull signals 52a and 52b are connected through in-series primary coil L1 and first matching network 56 resulting in a primary voltage (also called swing voltage) 54 across the coil L1. The coil L1 is inductively coupled with a secondary coil L2 which is in-series with a second matching circuit 64. A secondary voltage 62 is generated across the coil L2, and an output signal 66 is generated by the combination of the coil L2 and second matching circuit 64.

Figure 3:
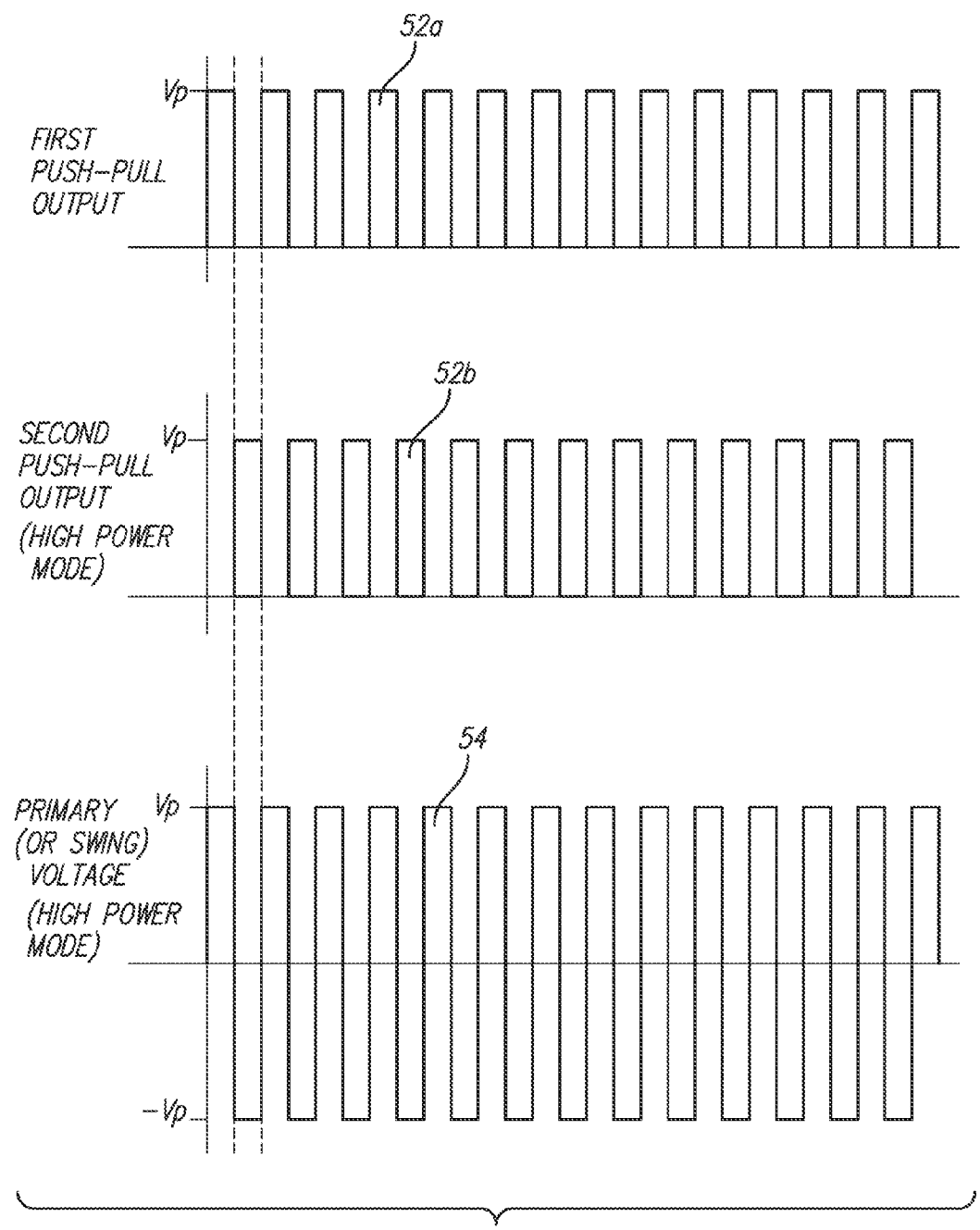
FIG. 3 depicts a first push-pull output, a second push-pull output, and a resulting primary (swing) voltage.

Plots of the first push-pull output 52a, the second push-pull output 52b, and the resulting primary voltage 54 are shown in FIG. 3. In the high power mode, the first push pull signal 52a and the second push pull signal 52b combine to generate a voltage swing of twice Vp across the primary coil L1 (FIG. 2). The coupling of the primary coil L1 with the secondary coil L2 results in an output signal with voltage 2Vp in the high power mode. In the low power mode, the second push-pull output is zero (i.e., set to ground) and the primary voltage resembles the first push-pull output 52a.

Figure 4A:
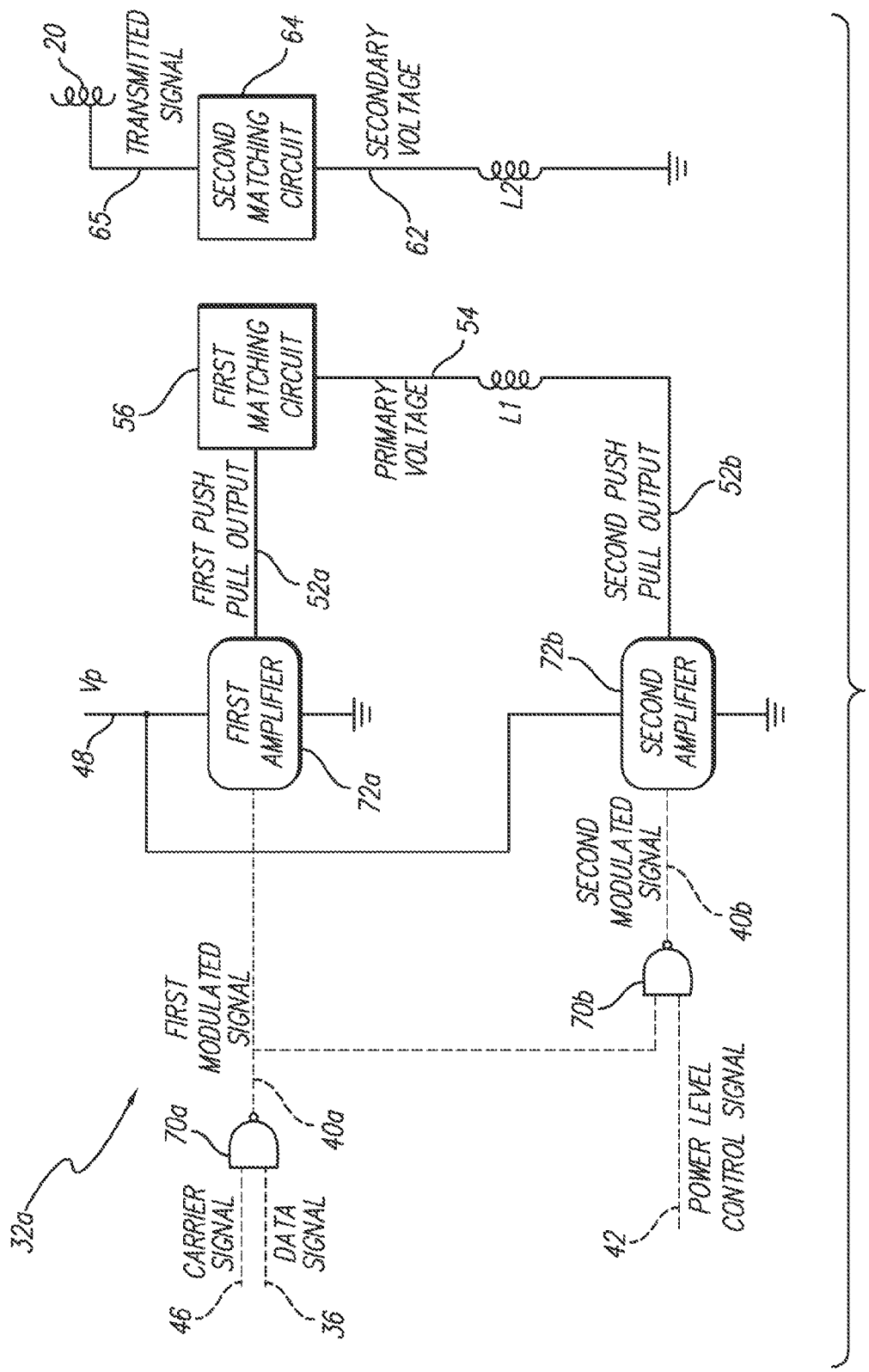
FIG. 4A shows an RF amplifier according to the present invention.

In known ICS systems 10 the processed signal may include both data and power. A digitally controlled RF amplifier 32a with wide dynamic range is shown in FIG. 4A. Such amplifier 32a is suitable for use within the signal processor 16 (FIG. 1)

to help generate the processed signal provided to the primary antenna 20 (FIG. 1). The amplifier 32a receives three digital signals and DC power. In the RF amplifier 32a, the periodic signal 34 in FIG. 2 comprises a carrier signal 46 which provides a high frequency carrier for RF power transmission. A data signal 36 (preferably 1 MHz) contains information that is transmitted by modulation of the carrier signal 46. The carrier signal 46 and data signal 36 are input to a first NAND 70a where a first modulated signal 40a is generated by modulating the carrier signal 46 by the data signal 36. The first modulated signal 40a is provided to a first amplifier 72a, and to a second NAND 70b. The power level control signal 42 is also provided to the NAND 70b. In the low power mode, a second modulated signal 40b generated by the NAND 70b is set to zero. In the high power mode, the second modulated signal 40b is set to the first modulated signal 40a with a 180 degree phase shift. The second modulated signal 40b is provided to a second amplifier 72b. The amplifiers 72a and 72b also receive a power signal 48 which preferably has 16 steps between 1.25 and 3 volts. While the example in FIG. 4A utilizes NANDs, any suitable logic circuit may be used.

Continuing with FIG. 4A, the first amplifier 72a generates the first push pull output 52a. The second amplifier 72b generates a second push pull output 52b 180 degrees out of phase with the first push pull output 52a when the power level control signal 42 is set to high power, and generates a zero output (i.e., is set to ground) when the power level control signal 42 is set to low power. The first push-pull output 52a and second push-pull output 52b are connected through the primary coil 58 and a capacitor C1 (preferably 500 pF), wherein the capacitor C1 performs as the first matching circuit 56 in FIG. 2. The primary coil L1 is inductively coupled with the secondary coil L2. The secondary coil L2 is connected to the antenna 20 through the second matching network 64. The ratio between the primary coil 58 and the secondary coil 60 may be 1:1, 1:2, or some other ratio, based on the power requirements and the component sizes of the amplifier 32a.

When the power level control signal 42 is set to high power, the first push pull output 52a and the second push pull output 52b combine (i.e., are enabled) resulting in the primary voltage (i.e., swing voltage) 54 present across the primary coil L1 which is twice the voltage of the power signal 48. When the power level control signal is set to low power, the second push pull output 52b is zero (i.e., ground), and the amplitude of the primary voltage 54 present across the primary coil L1 is equal to the voltage of the power signal 48. Thus, the amplifier 32a provides a high power mode, and a low power mode, controlled by the digital power level control signal 42, wherein the high voltage mode results in twice the voltage across the primary coil L1 as the low voltage mode.

Figure 4B:
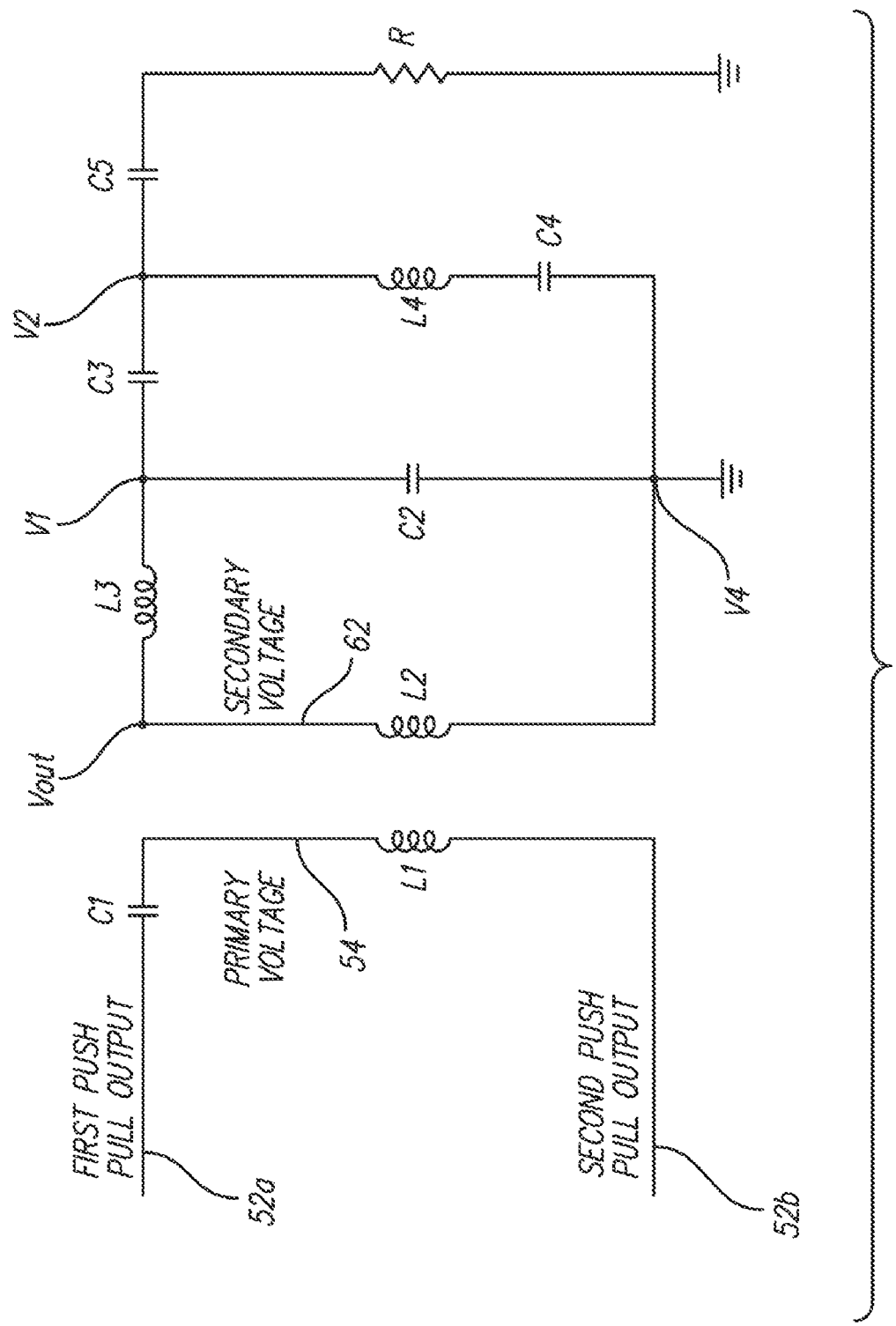
FIG. 4B shows an example of matching circuits suitable for use in the RF amplifier of FIG. 4A.

Examples of matching circuits 56 and 64 suitable for use in the amplifier 32a described in FIG. 4A are shown in FIG. 4B. The matching circuits of FIG. 4B are matched to coils L1 and L2 of 200 nH with a transformer ratio of 0.9. The first matching circuit 56 may comprise a capacitor C1 (preferably 500 pF). The second matching circuit 64 may comprise a circuit wherein the coil L2 is electrically connected between a fourth node V4 and a node Vout. The node V4 is electrically connected to ground. An inductor L3 (preferable 47 nH) is electrically connected between the node Vout and a first node V1. A second capacitor C2 (preferably 120 pF) is electrically connected between the node V1 and the node V4. A capacitor C3 (preferably 56 pF) is electrically connected between the node V1 and a second node V2. A fourth coil L4 (preferably 180 nH) and a fourth capacitor C4 (preferably 1200 pF) are electrically connected in series between the node V2 and the node V4. A fifth capacitor C5 (preferably 56 pF) and a resister R (preferably 50 ohms), which resister R represents a load, are electrically connected in series between the node V2 and ground. Those skilled in the art will recognize that other matching circuits may be substituted for the circuits described in FIG. 4B, and a wide dynamic range amplifier according to the present invention, including a different matching circuit, is intended to come within the scope of the present invention.

The carrier signal 46, data signal 36, and first modulated signal 40a (corresponding to the high power mode) are shown in FIG. 5. The carrier signal 46 is preferably a square wave, preferably between 20 Hz and 1000 Ghz, and more preferably 49 MHz, and preferably has amplitude equal to $V_p$, the voltage level of the power signal 48. The data signal 36 is a digital signal (i.e., is either zero or one), and is preferably at 1 MHz. The first modulated signal 40a is zero when the data signal 36 is zero, and is a copy of the carrier signal 46 elsewhere.

Figure 6A:
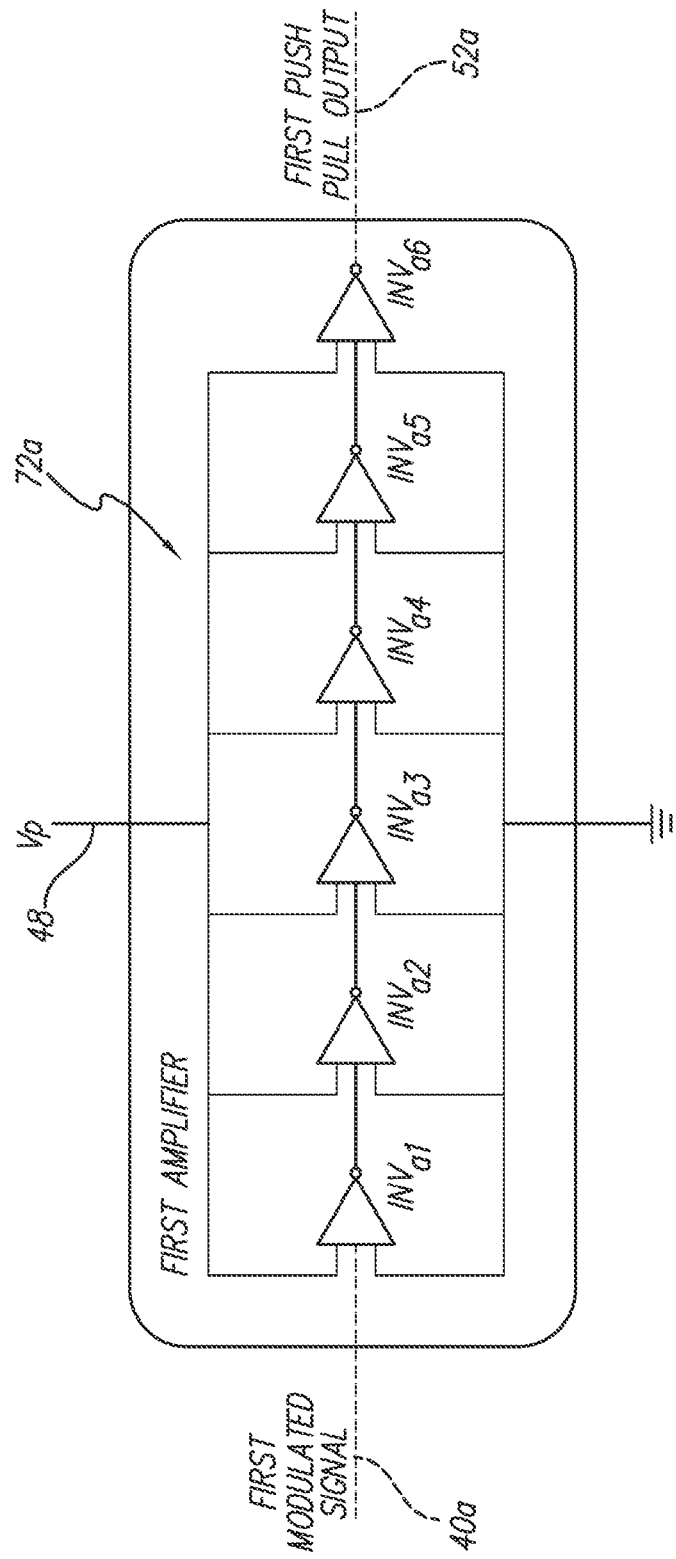
FIG. 6A shows details of a first amplifier comprising in-series invertors.
Figure 6B:
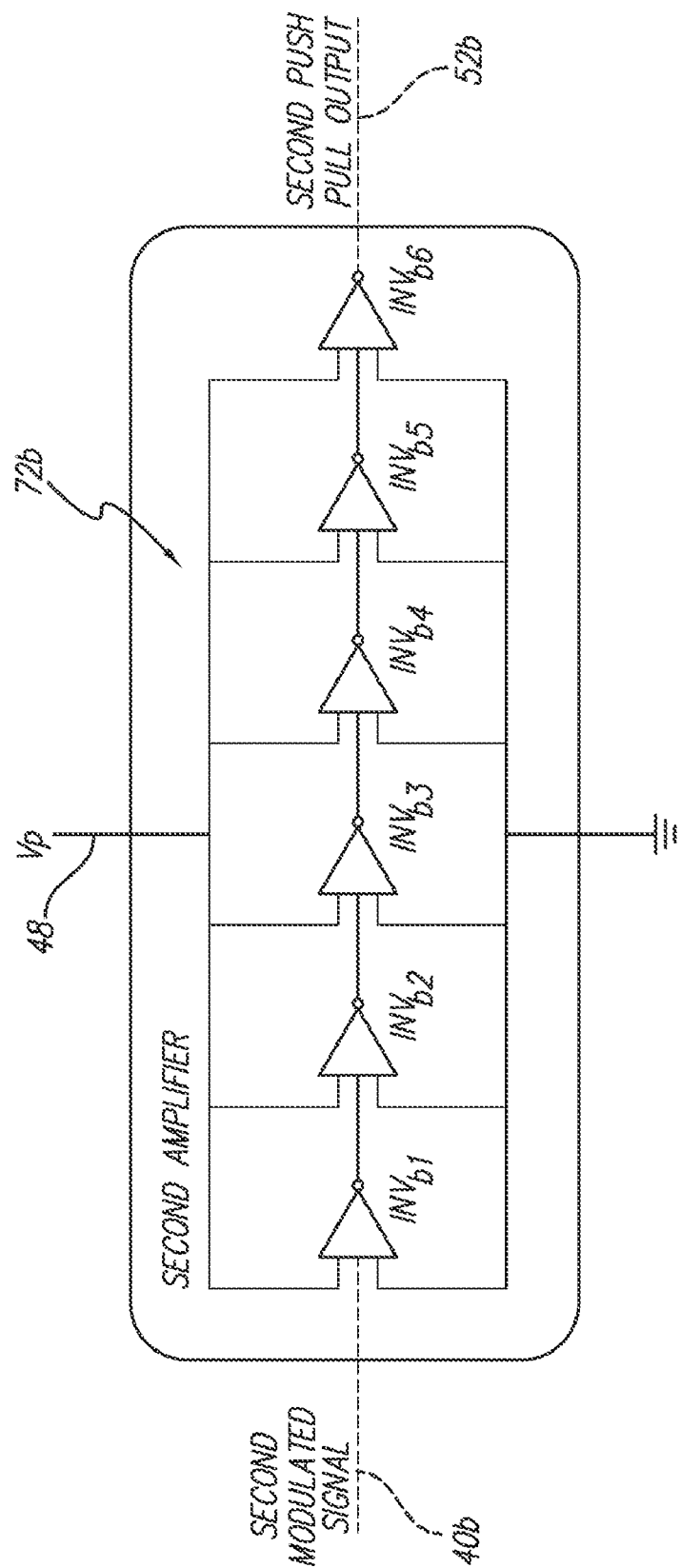
FIG. 6B shows details of a second amplifier comprising in-series invertors.

An example of the first amplifier 72a is shown in FIG. 6A, and an example of the second amplifier 72b is shown in FIG. 6B. The amplifier 72a receives the first modulated signal 40a as a control input, and the power signal 48 as a power source. The amplifier 72a comprises six stages (or invertors $INV_{an}$) preferably comprising in-series invertors $INV_{a1}$, $INV_{a2}$, $INV_{a3}$, $INV_{a4}$, $INV_{a5}$, and $INV_{a6}$, wherein each stage (after the first stage) receives the output of the previous stage as a control signal, and each stage receives the power signal 48 as a power source. The power provided at the output of each stage increases, and the output of the final stage (the first push-pull output 52a) provides the maximum designed power available from the power signal 48. Similarly, the example of the second amplifier 72b receives the second modulated signal 40b and the power signal 48, and processes the signals though six stages (or invertors $INV_{bn}$) preferably comprising in-series invertors $INV_{b1}$, $INV_{b2}$, $INV_{b3}$, $INV_{b4}$, $INV_{b5}$, and $INV_{b6}$, to generate the second push-pull output 52b. The number of stages may be varied as long as the resulting delays in the first push-pull output 52a and the second push-pull output 52b are substantially identical (i.e., within the normal tolerances of electrical components), and typically the first amplifier 72a and the second amplifier 72b will achieve identical delays by having the same number of stages.

Figure 7:
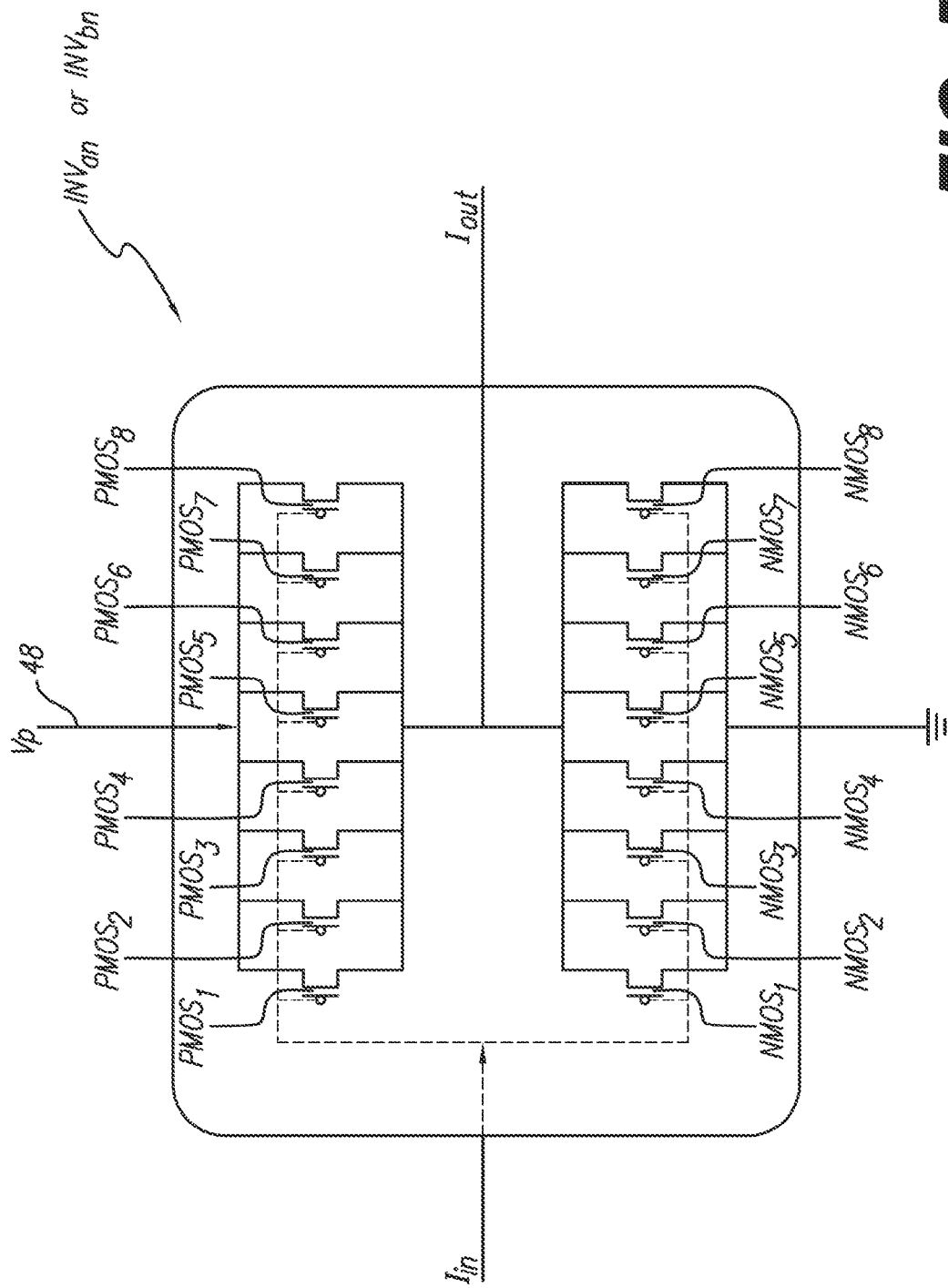
FIG. 7 depicts an invertor comprising PMOS and NMOS transistors.

An example INV** of a single stage of either the amplifier 72a or 72b is shown in FIG. 7. The stage, $INV_{an}$ or $INV_{bn}$, comprises eight PMOS transistors $PMOS_1$, $PMOS_2$, $PMOS_3$, $PMOS_4$, $PMOS_5$, $PMOS_6$, $PMOS_7$, and $PMOS_8$, and eight NMOS transistors $NMOS_1$, $NMOS_2$, $NMOS_3$, $NMOS_4$, $NMOS_5$, $NMOS_6$, $NMOS_7$, and $NMOS_8$. An input $I_{in}$ is a control signal for all of the switches in the stage. While the input $I_{in}$ is positive, the PMOS switches close, and the NMOS switches open, whereby the power signal 48 is connected to an output $I_{out}$. While the input $I_{in}$ is zero, the PMOS switches open and the NMOS switches close, thereby connecting the output $I_{out}$ to ground.

While the invention herein disclosed has been described by means of specific embodiments and applications thereof, numerous modifications and variations could be made thereto by those skilled in the art without departing from the scope of the invention set forth in the claims.

What is claimed is:

1. A wide dynamic range power amplifier comprising:
  a first output driver configured to receive a first input signal comprising a periodic signal and generate a first output signal comprising an amplified replica of said periodic signal;
  a second output driver configured to receive a second input signal comprising a substantially 180-degree-phase shifted version of said first input signal and generate a second output signal comprising an amplified replica of said second input signal;

a matching circuit configured to generate a power signal to be transmitted to an implantable device based on said first and second output signals, said matching circuit comprising a first matching network and a primary coil together residing in-series between said first and second output drivers, wherein said first matching network receives said first output signal and said primary coil receives said second output signal, and a second matching network in-series with a secondary coil that is inductively coupled to said primary coil, said second matching network and said secondary coil together being configured to cooperate with said first matching network and said primary coil to generate said power signal; and a processor configured to receive a control signal input indicating one of a low power mode and a high power mode;

wherein said processor is further configured to set said second output signal to zero when said control signal input indicates said low power mode.

2. The amplifier of claim 1, further comprising a transmitting coil connected to the matching circuit and configured to transmit said power signal to said implantable device.

3. The amplifier of claim 2, wherein said transmitting coil is configured to transmit said power signal to said implantable device by transmitting said power signal to a cochlear stimulator.

4. The amplifier of claim 1, wherein said power signal comprises a first power level when said control signal indicates said low power mode and a second power level substantially equal to four times said first power level when said control signal indicates said high power mode.

5. The amplifier of claim 1, wherein said processor is configured to generate said substantially 180-degree-phase-shifted version of said first input signal.

6. The amplifier of claim 1, wherein each of said output drivers comprises a plurality of in-series inverter stages.

7. The amplifier of claim 6, wherein each of said plurality of in-series inverter stages comprises a bank of PMOS transistors and a bank of NMOS transistors.

8. The amplifier of claim 1, wherein said processor comprises a NAND gate.

9. The amplifier of claim 1, wherein said periodic signal comprises a data signal modulated with a carrier signal.

* * * * *